United States Patent [19]

Keating et al.

[11] Patent Number: 5,339,828

[45] Date of Patent: Aug. 23, 1994

[54] APPARATUS AND METHOD FOR TAKING CULTURES ENDOSCOPICALLY

[76] Inventors: Daniel J. Keating, 231 Berteau, Elmhurst, Ill. 60126; Natalie R. Siska, 1255 Elder Rd., Homewood, Ill. 60430

[21] Appl. No.: 8,709

[22] Filed: Jan. 25, 1993

[51] Int. Cl.⁵ .............................................. A61B 10/00
[52] U.S. Cl. ................................... 128/759; 128/749; 128/756; 604/1
[58] Field of Search ............... 128/749, 756, 759, 764, 128/760, 768, 750, 897; 206/209; 435/292; 604/43, 1

[56] References Cited

U.S. PATENT DOCUMENTS

| | | | |
|---|---|---|---|
| 3,368,549 | 2/1968 | Barr et al. | 128/759 |
| 3,450,129 | 6/1969 | Avery et al. | 128/2 |
| 3,800,781 | 4/1974 | Zalucki | 128/749 |
| 3,857,384 | 12/1974 | Watson | 128/749 |
| 4,030,978 | 6/1977 | Abramson | 195/75 |
| 4,312,950 | 1/1982 | Snyder et al. | 128/759 |
| 4,586,604 | 5/1986 | Alter | 206/209 |
| 4,653,510 | 3/1987 | Koll | 128/756 |
| 4,877,037 | 10/1989 | Ko et al. | 128/756 |
| 5,129,402 | 7/1992 | Koll et al. | 128/759 |

*Primary Examiner*—Lee S. Cohen
*Assistant Examiner*—Brian M. Green
*Attorney, Agent, or Firm*—Wood, Phillips, VanSanten, Hoffman & Ertel

[57] ABSTRACT

An apparatus is provided to take a culture sample from within a body cavity including an elongate extension having a swab capable of obtaining the culture sample. Structure is provided for shielding the swab to assist introduction thereof into a body cavity. The extension and swab are exposed to the cavity to obtain the sample. The sample is then isolated from contaminants by retracting the swab with the sample thereon into the shielding structure whereupon the sample is transferred to a culture medium without contaminating the sample.

33 Claims, 4 Drawing Sheets

APPARATUS AND METHOD FOR TAKING CULTURES ENDOSCOPICALLY

FIELD OF THE INVENTION

This invention relates to surgical procedures and, more particularly, to a method and an apparatus to obtain a culture sample through an endoscopic cannula and transfer the sample to a culture medium without contaminating the sample.

BACKGROUND OF THE INVENTION

Presently, culture samples are obtained by the use of a stick and swab directed into a body cavity into contact with an internal mass from which a sample is to be taken. Access to the body cavity is generally obtained by cutting through tissue to provide an opening sized to allow performance of a conventional surgical procedure. A conventional incision is generally large enough to permit introduction and withdrawal of the swab without the swab's inadvertently contacting other masses or the tissue surrounding the incision.

Once the stick and swab were removed with the culture sample thereon, the sample had to be immediately transferred to a container having culture medium therein to avoid possible contamination of the sample and to prevent clinicians from inadvertently coming in contact with the sample.

In performing endoscopic surgery, an incision or puncture hole is made in a patient to admit a cannula which serves as a conduit for the introduction of selected surgical instruments into a body cavity. The body cavity in which the operation is performed is filled with a gas to expand the surrounding tissue to create a suitably-sized operating space.

Heretofore, surgeons have foregone the taking of culture samples through incisions or puncture holes used in endoscopy due to the constraints of the incision and other complicating factors peculiar to endoscopy.

During endoscopy, it is important to confine the gas to maintain the tissue surrounding the cavity in a distended state. If the tissue collapses, access to the desired region may be impaired or altogether precluded. Insertion of the swab could potentially damage internal organs. However, heretofore, no way has been known to seal the cannula while at the same time preventing contamination of a sample withdrawn therethrough. That is, if provision is made to closely seal around the stick and swab, this same sealing structure would necessarily contact, and thereby contaminate the sample as well as potentially separate the sample from the swab.

In the event of an incomplete seal, the gas, blood, and other bodily fluids in the cavity can rush over and past the sample to potentially contaminate the sample.

The use of a stick and swab through an endoscopic cannula presents other problems with regards to control of the stick and swab. There is the potential that during the procedure the stick and swab may be dropped into the cannula and cavity.

SUMMARY OF THE INVENTION

The present invention is specifically directed to overcoming the above-enumerated problems in a novel and simple manner.

According to the invention an apparatus is provided to take a culture sample from within a body cavity through an opening, as through an endoscopic cannula, the apparatus including an elongate extension having a swab thereon to pick up and transfer the culture sample, structure for shielding the swab to facilitate introduction thereof into a body cavity, and cooperating structure on the shielding structure and at least one of the elongate extension and swab to guide relative movement thereof between (a) a shielded position, which facilitates transportation of the swab into and out of the body cavity, and (b) an exposed position wherein the swab is exposed to allow it access to the body cavity from which the culture sample is to be taken.

Preferably, the shielding structure is an introducer tube which has a length extending between proximal and distal ends and a wall defining a through passageway. The introducer tube and the cannula are configured so that the outside diameter of the introducer tube is less than the inner cannula diameter to allow the tube to be directed through the cannula to an operative position wherein the swab can access the cavity and take a sample therefrom. Preferably, the cooperating structure is a surface on the introducer tube wall which frictionally engages and guides one of the extension and swab lengthwise relative to the introducer tube between the shielded and exposed positions. Further, the cooperating structure can include a stopper on the extension to engage the surface of the introducer tube and move guidingly lengthwise thereagainst. The stopper can also include sealing structure to block the tube passageway and prevent the escape of gas therefrom with the extension and swab inserted therein. The sealing structure can alternatively be placed on the tube.

Another aspect of the invention is the provision of structure on the extension to maintain the swab in the shielded position and limit lengthwise movement thereof relative to the introducer tube allowing for limited swab movement from the proximal to the distal end of the tube. This allows a sample to be taken and isolated from contaminants during retraction from the cavity and transfer to a culture medium. In one exemplary embodiment, a removable boss is provided on the extension having an outside diameter slightly larger than the inner diameter of the tube wall, thereby maintaining the swab in the shielded position. Preferably, the proximal end of the tube is an enlarged annular end portion which bears against the boss when the extension and swab are moved lengthwise relative to the introducer tube so that the distal end of the tube surrounds the swab in the shielded position.

Another aspect of the invention is the provision of structure on the extension to limit lengthwise movement of the swab in its exposed position. In one exemplary embodiment, a collar member is provided on the extension having an outside diameter slightly larger than the inner diameter of the tube wall so that the collar member bears against the proximal end of the tube when the boss is removed and the extension is slid lengthwise through the tube so that the swab is in the exposed position.

In a preferred form, the boss is positioned between the stopper on the extension and the collar member with the stopper positioned between the swab and the removable boss on the extension with the swab in the shielded position. Further, in the exposed position, the stopper is positioned between the swab and the collar on the extension.

Another aspect of the invention is the provision of a severable extension and tube so that the tube containing the extension and swab with the culture sample thereon can be transferred to a culture medium and thereafter snapped off leaving the swab and shortened extension and tube in a sealed culture medium without contaminating the culture sample. Alternatively, only the extension need be snapped off.

Another aspect of the invention is the provision of structure on the tube for regulating the position of the tube inserted in the cannula. In one exemplary embodiment, a depth collar is provided on the tube and bears against the cannula so that the tube extends a predetermined distance into the cavity when the tube is inserted into the cannula.

The present invention also contemplates a method for obtaining a culture sample from within a body cavity through an opening in tissue, as through an endoscopic cannula, the method including the steps of introducing an elongate extension having a swab thereon into a cannula, exposing the swab through the cannula so that it has access to a cavity from which a sample is to be taken, isolating the sample from contaminants, and transferring the sample to a culture medium without contaminating the sample.

Another aspect of the invention is to include the step of directing the extension and swab into a hollow passageway of an introducer tube having proximal and distal ends. The tube facilitates transportation of the swab into and out of the body cavity while isolating the sample from contaminants. Alternatively, the extension and swab are provided within the tube passageway during manufacture.

In a preferred form, the step of exposing the swab to the cavity is effected by removal of a boss on the extension which bears against the proximal tube end and sliding the extension lengthwise through the tube until the swab is sufficiently exposed to the cavity to allow the taking of a sample.

Another aspect of the invention is to include the step of providing a collar on the extension so that when the extension is slid lengthwise through the tube with the swab exposed sufficiently to the cavity to allow the taking of a sample, the collar abuts the proximal tube end.

Another aspect of the invention is to include the step of isolating the sample from contaminants and transporting the sample from the cavity to a culture medium without contaminating the sample by retracting the swab to a position within the distal end of the tube and then placing the tube with the extension therein in a culture medium. After transfer to the culture medium, the tube with the extension therein can be broken off, leaving the uncontaminated swab in a culture medium which can then be sealed. Alternatively, the extension can be slid lengthwise to the exposed position in the container with only the extension being snapped off therein.

DETAILED DESCRIPTION OF THE DRAWINGS

Figure 1:
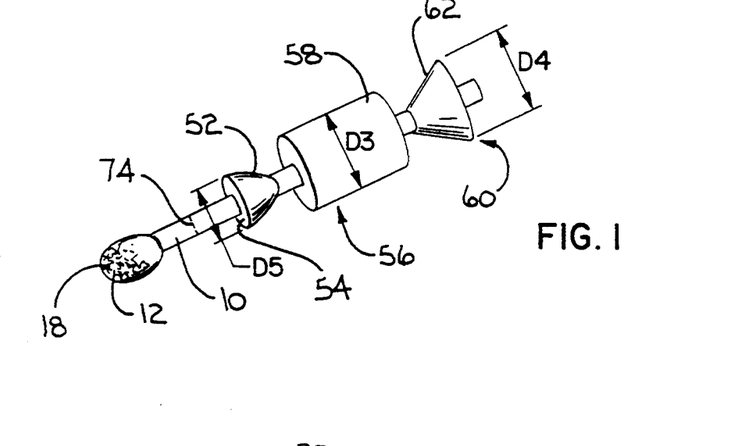
FIG. 1 is a perspective view of an elongate extension with a swab thereon and a stopper, removable boss, and collar member mounted on the extension according to the invention.
Figures 6, 7:
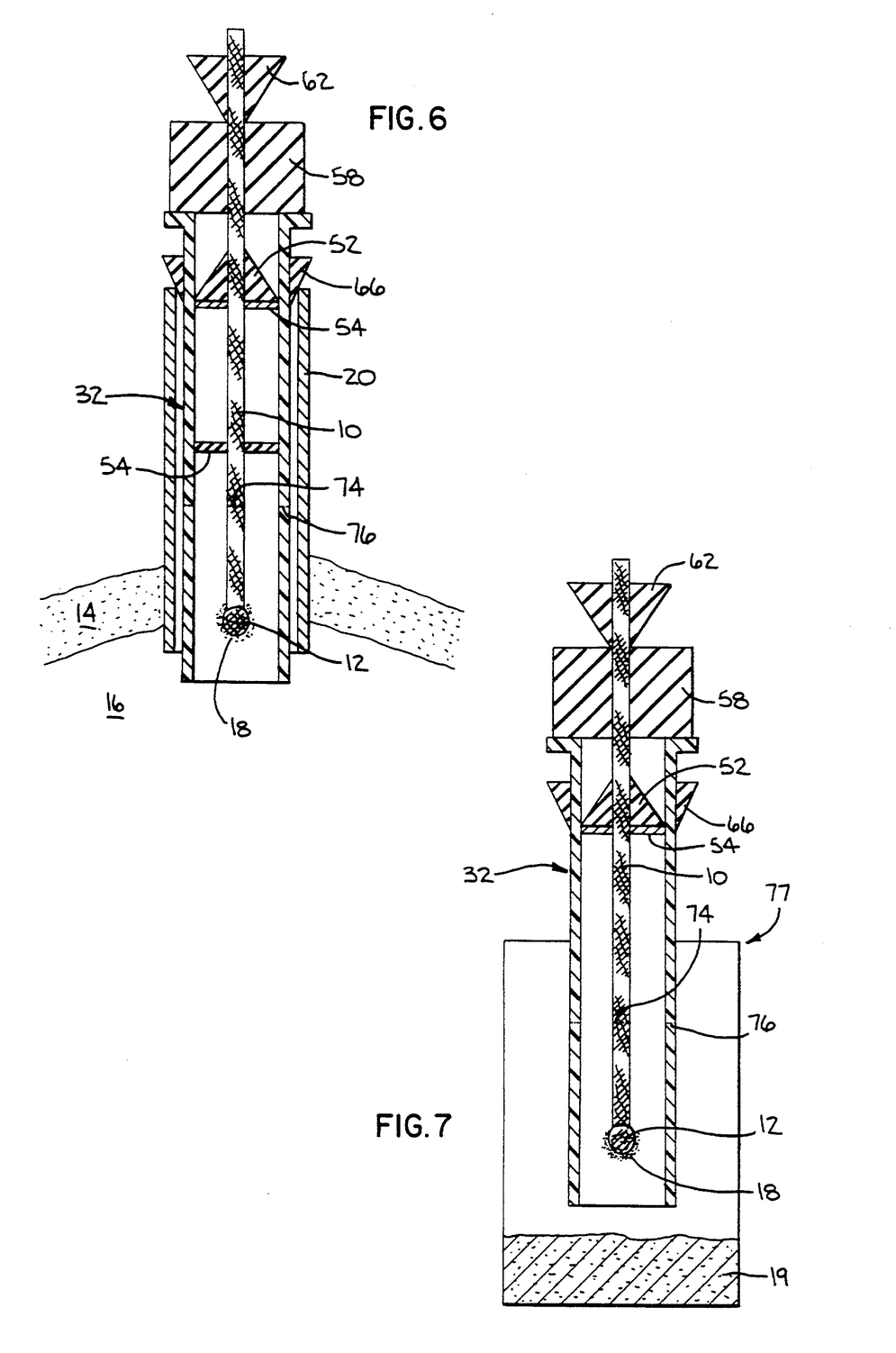
FIG. 6 is a section view as in FIG. 4 with the extension and swab having a sample thereon retracted into the introducer tube.
FIG. 7 is a section view of the swab with the sample thereon in a container having a culture medium therein.
Figure 8:
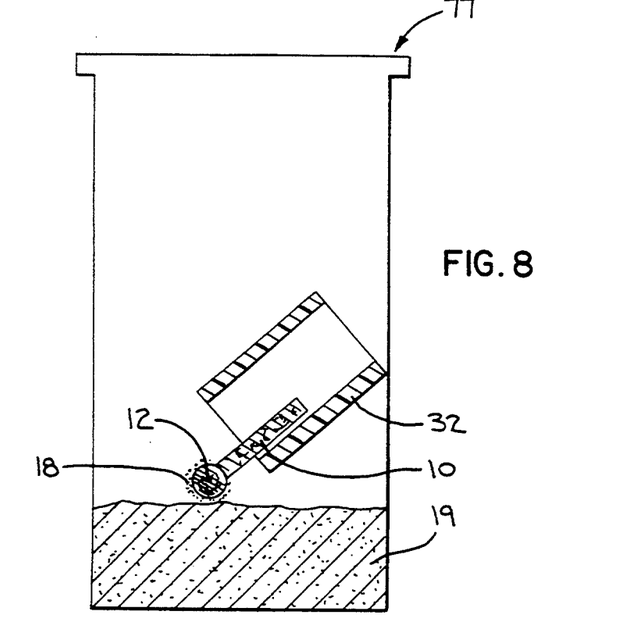
FIG. 8 is a section view as in FIG. 7 with the extension and introducer tube broken off to allow sealing of the container.

FIG. 1 shows an elongate extension 10 with an absorbent swab 12 thereon. The extension 10 can be either a stick or a flexible guidance cable or any other suitable tool capable of obtaining a culture sample 18. The swab 12 is capable of picking up and retaining a culture sample 18, shown in FIG. 5. The extension 10 enables the swab 12 to be inserted a substantial distance into a body cavity 16 to access a mass therein from which the sample 18 is to be taken. The swab 12 is used to pick up the culture sample 18 from within the body cavity 16 and transfer it to a culture medium 19 (FIGS. 7 and 8).

Prior to this invention, the swab 12 had was commonly inserted into an incision large enough to insure that the culture sample 18 obtained on the swab 12 did not contact any possible sources of contamination when being inserted into and removed from the body cavity 16. Secondly, the sample 18 was normally quickly encased so as not to become contaminated during transfer from externally of the body cavity to the culture medium 19 and to prevent clinicians from coming in contact with the sample 18.

Figure 3:
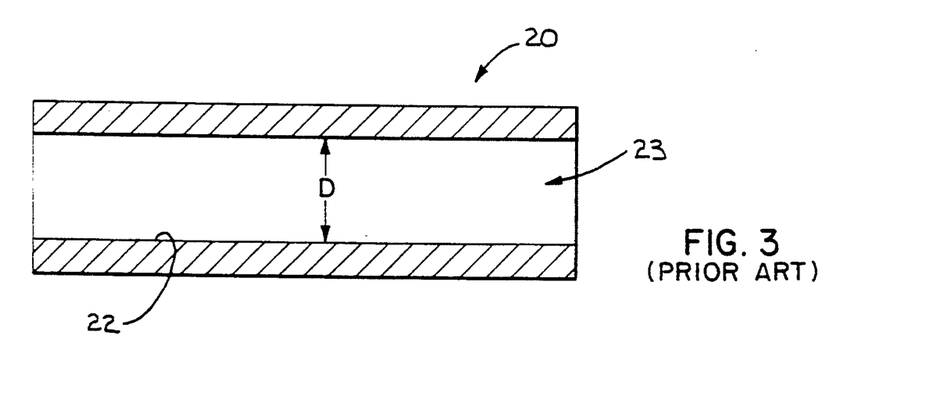
FIG. 3 is a section view of a conventional endoscopic cannula through which the introducer tube can be directed.

FIG. 3 illustrates a conventional cannula 20 usable with the present invention. The cannula 20 has an inside wall surface 22 defining a passageway 23 with an inside diameter D. The cannula 20 permits surgical tools to communicate with the body cavity 16 through a small incision (not shown) made in a body tissue 14.

Generally, shielding means 30 (FIG. 2) is provided to facilitate insertion of the swab 12 through the cannula 20 into the body cavity 16 to procure the culture sample 18 from the body cavity 16 without contamination of the sample.

Figure 2:
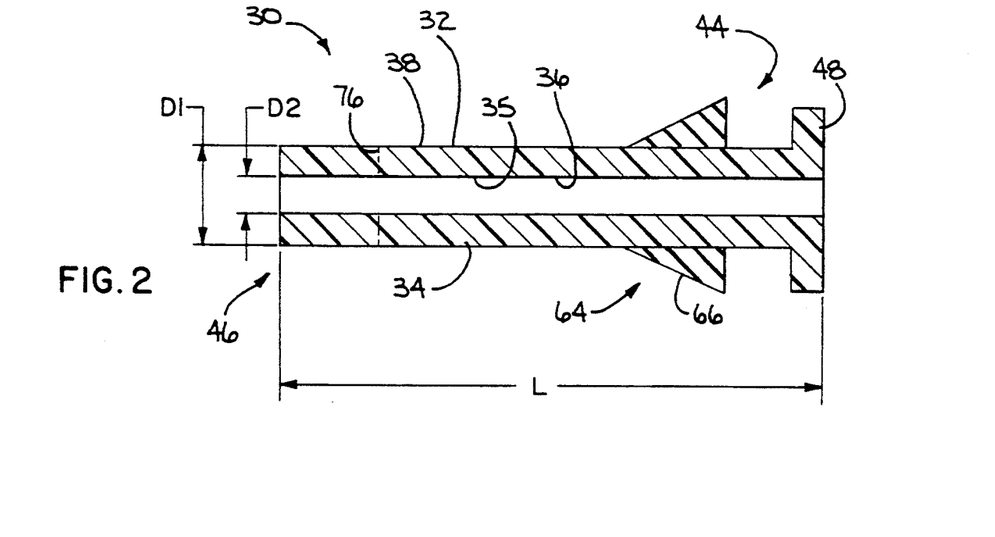
FIG. 2 is a section view of an introducer tube for receiving the extension with the swab thereon and selectively shielding the swab.

More particularly, the shielding means 30 includes an introducer tube 32 shown in FIG. 2. The introducer tube 32 has a wall 34 that defines a through passageway 36. The introducer tube 32 has a length L and proximal and distal ends, 44 and 46, respectively.

Figures 4, 5:
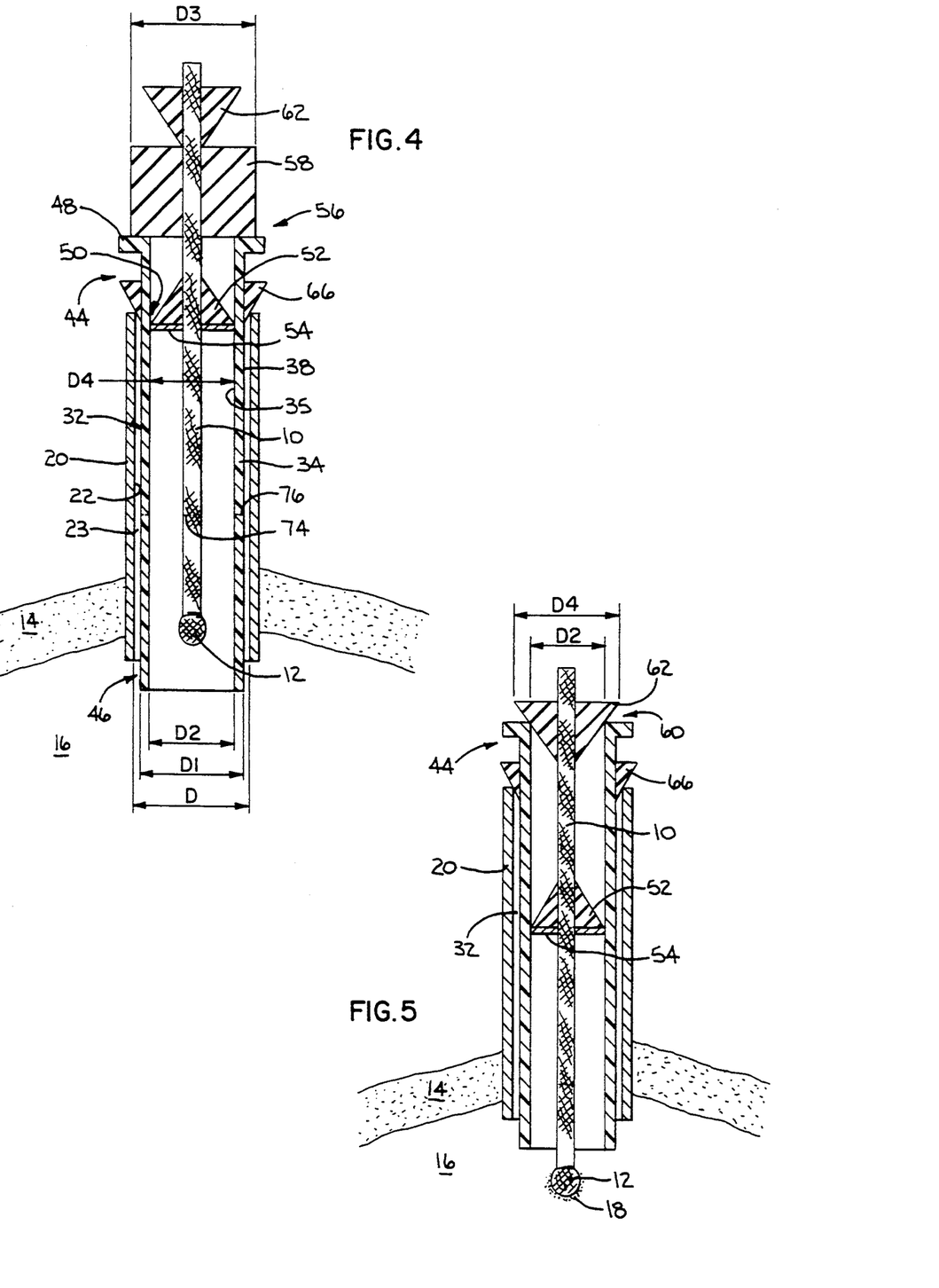
FIG. 4 is a section view of the cannula in operative position through body tissue with the extension and swab within the introducer tube in a shielded position.
FIG. 5 is a section view as in FIG. 4 with the extension and swab in an exposed operative position in which a sample can be taken.

As seen in FIGS. 2 and 4-7, the shielding means 30, and more specifically the introducer tube 32, and the extension 10 and swab 12 are provided with cooperating means 50 thereon to allow relative unsubstructed guided movement within the through passageway 36 of the tube 32 between shielded and exposed positions. As seen in FIG. 4, the wall 34 of the introducer tube 32 has an outside surface 38 with a diameter D1 and an inner surface 35 with a diameter D2. The outside diameter D1 of the introducer tube wall 34 is less than the inner cannula diameter D allowing the introducer tube 32 to be directed through the cannula passageway 23 to an operative position within the body cavity 16 while preventing the swab 12 from inadvertently contacting the tissue 14 surrounding the incision.

The introducer tube 32 can be either disposable or reusable. If the tube 32 is disposable, then the tube 32 can be manufactured with the extension 10 and swab 12 therein. If the tube 32 is reusable, then the extension 10 and swab 12 can be both inserted into the tube 32 and removed therefrom after manufacture. Further, a reusable tube 32 should preferably be stainless steel, while a disposable tube 32 should be formed from a material capable of being snapped when provided with perforations as more fully described herein.

In any type of surgical procedure using a flexible type of scope or cannula such as in gastroscopy, bronchoscopy, thoracoscopy, colonoscopy, and choledochoscopy, the tube 32 must also be made from a hollow flexible type material with the extension 10 likewise made from a flexible material such as a coaxial cable or guidance cable.

The extension 10 and the swab 12 in the introducer tube 32 are guided by the cooperating means 50 relative to one another. More specifically, the cooperating means 50 includes a surface 35 of the tube wall 34 which frictionally engages one of the extension 10 and swab 12. This allows the extension 10 and swab 12 to be moved guidingly lengthwise relative to the introducer tube 32 between a shielded and an exposed position, shown in FIGS. 4 through 6, respectively.

The cooperating means 50 can also include a stopper 52 on the extension 10 which engages the surface 35 of the tube 32, as seen in FIG. 4. The stopper 52 has a diameter D5 substantially equal to the diameter D2 of the inner surface 35 of the tube 32. This permits the extension 10 and swab 12 to move lengthwise in the tube 32 while the stopper 52 bears against the surface 35 of the tube wall 34 to guide lengthwise movement of the extension 10 and swab 12 between the shielded and exposed positions (FIGS. 4–6).

The stopper 52 can include sealing means 54 for sealing the introducer tube passageway 36 when the extension 10 and swab 12 are inserted therein. The sealing means can be any annular element that prevents the escape of gas from the body cavity 16. By fitting the stopper 52 and sealing means 54 closely around the extension 10, the possibility of separating the sample 18 from the swab 12 when retracting the sample 18 into the tube 32 is eliminated (FIG. 6).

Alternatively, the sealing means 54 can be provided on the introducer tube 32. Further, the sealing means 54 can be provided both on the introducer tube 54 and on the extension 10 to furnish additional insurance against any possible escape of gas from the cavity 16.

When a disposable tube 32 is used, it is preferable to use a resilient, fixed stopper 52 on the extension 10, the stopper 52 allowing lengthwise movement between shielded and exposed positions but preventing removal of the extension 10 and swab 12 from the tube 32 at its proximal end 44. This function can be obtained by providing the tube 32 at the proximal end 44 thereof with an element having an inwardly projecting lip (not shown) which can contact the stopper 52 thereby preventing removal of extension 10 and swab 12 from the tube 32.

When a reusable tube 32 is used, it is preferable to use a flexible stopper 52 on the extension 10. With a flexible stopper 52, it is possible to insert the extension 10 into the tube 32 and remove it therefrom. If a flexible stopper 52 is used, then the diameter D5 can be slightly larger than the diameter D2 of the tube 32 as the stopper 52 is deformable when inserted into the tube 32 at its proximal end 44.

Generally, the introducer tube 32 has regulating means 64 to control the position of the introducer tube 32 within the cannula 20. Specifically, the regulating means 64 includes a depth collar 66 which abuts the portion of the introducer tube 32 which remains external of the patient thereby regulating the depth to which the introducer tube 32 descends into the body cavity 16.

It is apparent that the introducer tube 32 and extension 10 can be made to a variety of sizes to accommodate the surgical procedure being performed and the proficiency of the surgeon performing the procedure. For example, in pelviscopic procedures, the tube 32 will normally be approximately 45 cm in length; in laparoscopy, approximately 30 cm; in thoracoscopy, approximately 18 cm; and down to approximately 8 cm or smaller for procedures in the sinus cavity and up to approximately 200 cm or larger when the surgical procedure is done with a flexible type of scope or cannula. It is desirable for the extension 10 to be at least 4–5 cm longer than the tube 32 it is being used with to accommodate the maintaining means and limiting means described herein and to enable the surgeon to control the extension 10 within the tube 32 and ultimately the body cavity 16. The outer diameter D1 of the tube 32 can range anywhere from approximately 3–20 mm, depending on the cannula 20 size although the regulating means 64 allows the tube 32 to be used with a variety of larger-sized cannulas 20.

The shielded position, as seen in FIG. 4, is preserved by a maintaining means 56 on the extension 10. More specifically, the maintaining means include a removable boss 58 on the extension 10 having an outside diameter D3. The boss outside diameter D3 is slightly larger than the inner diameter D2 of the tube wall 34 to assure contact between the two when the extension 10 is directed through the tube 32 thereby assuring access to the extension 10 even if it is dropped by the surgeon while inserted in the tube 32.

Due to the difference in diameters between the boss 58 and the tube wall 34, when mounted on the extension 10, the boss allows the extension 10 and swab 12 to be inserted into the tube 32 until the boss 58 abuts the proximal end 44 of the tube 32. To further assure this abutting relationship, the proximal end 44 of the tube 32 can have an enlarged annular end portion 48. Hence, when the boss 58 abuts the enlarged annular end portion 48, the distal end 46 of the tube 32 surrounds the swab 12 in the shielded position.

In addition, when the boss 58 is in an abutting relationship with the enlarged end portion 48 of the tube 2, the surgeon can grip the boss 58 and move the extension 10 and tube 32 in conjunction with one another in the cannula 20 so that the distal end 46 of the tube 32 is in proper position within the cavity 16 to access a specific sample 18 without the danger of losing the extension 10 and the swab 12 in the cavity 16. If by any chance the extension 10 and swab 12 are lost in the cavity 16, they can be provided with radio-opaque strips so that they are visible in an X-ray of the cavity 16. Further, the extension 10 should be made from pyrogenic materials that do not conduct heat and will not catch fire so that when, for example, the surgeon decides to take a sample 18 from an area that has just been cauterized, the surgeon can do so safely.

When the boss 58 is removed from the extension 10, the extension 10 can be moved downward to the exposed position, shown in FIG. 5, in which the swab 12 has access to the body cavity 16 while not contacting any tissue 14 surrounding the incision when extended through the incision.

Generally, limiting means 60 is mounted on the extension 10. More specifically, the limiting means 60 include a collar 62 having a collar diameter D4. The collar diameter D4 is slightly larger than the inner diameter D2 of the inner surface 35 of the tube wall 34. Hence, the collar 62 can bear against the proximal end 44 of the tube 32 when the swab 12 is in the exposed position limiting the depth which the swab 12 can descend to in the body cavity 16. The collar 62 prevents the extension 10 and swab 12 from being lost in the body cavity 16 if accidentally dropped by the surgeon. Furthermore, the collar 62 permits the swab 12 to enter the body cavity 16 only a predetermined distance depending on the location of the collar 62 on the extension 10 and the relative lengths between the extension 10 and the introducer tube 32.

When the swab 12 is in the exposed position, a culture sample 18 can be procured from the body cavity 16. To transfer the sample 18 to a culture medium 19 (FIGS. 7 and 8), the extension 10 and swab 12 are retracted to the shielded position (FIG. 6) and removed from the cannula 20 simultaneously preventing the swab 12 from contacting tissue 14 surrounding the incision and isolating the sample 18 from contaminants. At this point, the removable boss 58 can be remounted on the extension 10 to assure that the swab 12 is maintained in the shielded position. The extension 10 and the introducer tube 32 (disposable) are provided with perforations 74 and 76, respectively, so that when the swab 12 is in the shielded position, the perforations 74 and 76 are generally in line with one another, as shown in FIGS. 6 and 7.

Figure 9:
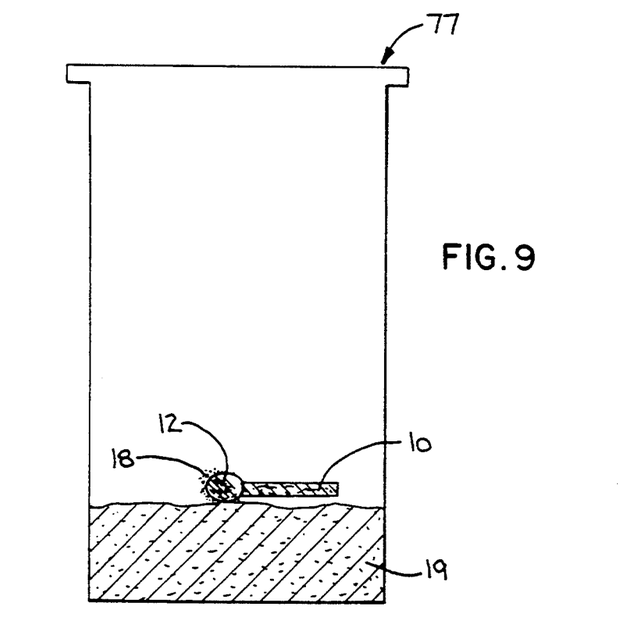
FIG. 9 is a section view as in FIG. 7 with only the extension broken off to allow sealing of the container.

The perforations 74 and 76 of the extension 10 and tube 32 allow the tube 32 with the swab 12 and sample 18 therein to be snapped off into a culture medium 19, as illustrated in FIG. 8. If a reusable tube 32 is used, then only the extension 10 is snapped off into the culture medium 19, as seen in FIG. 9. By provision of the introducer tube 32, and perforations 74 on the extension 10 and perforations 76 on the disposable tube 32 when it is used, the culture sample 18 can be procured and transferred to a culture medium 19 without contaminating the culture sample 18.

Furthermore, while the tube 32 has been described as being particularly useful for endoscopic procedures, it is apparent that the tube 32 can also be used to obtain a culture sample 18 through a conventional incision while still performing the dual functions of isolating the sample 18 from contaminants and facilitating transfer thereof to a culture medium 19.

A method for obtaining culture sample through an endoscopic cannula and transferring the sample to a culture medium without contaminating the sample will now be described.

An incision (not shown) is made in the tissue 14. The endoscopic cannula 20 is directed through the incision so that surgical instruments controlled from a position externally of the patient can communicate with the body cavity 16. The elongate extension 10 and swab 12 can be introduced into the cannula 20 by way of the introducer tube 32. The extension 10 has the removable boss 58 mounted thereon. At this point, the swab is in the shielded position, as illustrated in FIG. 4.

The boss 58 is removed from the extension 10 and the extension 10 is slid lengthwise through the tube 32 exposing the swab 12 to the body cavity 16, as shown in FIG. 5. The swab 12 can be extended only as far as the collar 62 permits since the collar 62 is mounted on the extension 10 so that it can abut the proximal end 44 of the introducer tube 32 limiting the depth to which the swab 12 can descend to in the body cavity 16. The removal of the boss 58 allows the swab 12 to be maneuvered along the length of the extension 10 occupied by the removed boss 58 until the collar 62 abuts the proximal end 44 of the tube 32 to obtain a culture sample 18 thereon.

Once the culture sample 18 is obtained, the swab 12 with the sample 18 thereon is retracted into the tube 32 into the shielded position, as seen in FIG. 6, thereby isolating the sample from any possible source of contamination when withdrawing the extension 10 and swab 12 from the body cavity 16 through the small incision in the tissue 14. At this point, the boss 58 may be returned to its position on the extension 10 maintaining the swab 12 securely in the shielded position during retraction of the tube 32 from the body cavity 16 and transfer of the tube 32 with the extension 10 and swab 12 therein to the culture medium 19 (FIG. 7).

When the boss 58 is replaced on the extension 10, the perforations 74 and 76 on the extension 10 and the disposable tube 32, respectively, are aligned with one another (FIGS. 6 and 7). The tube 32 with the extension 10, swab 12, and sample 18 therein are transferred to a container 77 having a culture medium 19 therein.

The container 77 is then opened and the extension 10 and swab 12 with the sample 18 thereon are placed in the container 77, as seen in FIG. 7. The perforations 74 are 76 allow the extension 10 and tube 32 to be snapped easily so that only a portion of the extension 10 and tube 32 are left in the container 77 along with the swab 12 and the uncontaminated culture sample 18, as shown in FIG. 8. The container 77 can then be sealed with the uncontaminated sample 18 therein.

When the tube 32 is reusable, the tube 32 does not include any perforations as it is generally stainless steel which is not breakable for these purposes. The method with a reusable tube 32 is only dissimilar than the one previously described in that upon transferring the sample 12 within the tube 32 to the container 77, the extension 10 is slid lengthwise through the tube 32 exposing the swab 12 in the container 77 so that the extension 10 can be snapped off at its perforations 74 whereby only a portion of the extension 10 is left in the container along with the swab 12 and the uncontaminated culture sample 18. Both of these methods permit the culture sample 18 to be obtained and transferred with relative ease while isolating it from contaminants.

As discussed earlier, it is also apparent that, while particularly adapted to be useful in endoscopic procedures, the tube 32 can also be used to obtain a sample when a conventional incision is used. This method is the same in all respects as the method previously described except that with the larger incision, an endoscopic cannula is not employed and instead, the tube 32 is inserted directly into the body cavity 16.

The foregoing disclosure of specific embodiments is intended to be illustrative of the broad concepts comprehended by the invention.

We claim:

1. In combination:

a cannula having an opening therethrough; and an apparatus to take a culture sample from within a body cavity through the cannula opening, said apparatus comprising:

means for collecting and transferring a culture sample from within a body cavity, said collecting and transferring means including an elongate extension with a swab thereon, said elongate extension facilitating introduction of the swab into a body cavity;

means for shielding the swab to facilitate introduction thereof into a body cavity, said shielding means being movable into said cannula opening; and cooperating means on the shielding means and at least one of the elongate extension and swab for guiding relative movement thereof between a) a shielded position wherein transportation of the swab into and out of a body cavity is facilitated and b) an exposed position wherein the swab is exposed sufficiently to allow it to access a body cavity from which a culture sample is to be taken.

2. The combination of claim 1 wherein the elongate extension comprises one of a stick and a flexible cable.

3. The combination of claim 1 wherein the shielding means comprises an introducer tube having a length and a proximal and a distal end, said introducer tube having a wall defining an introducer tube through passageway.

4. The apparatus of claim 3 wherein the cooperating means comprises a surface on the introducer tube wall which frictionally engages and guides the one of the elongate extension and swab lengthwise relative to the introducer tube between the shielded and exposed positions.

5. The apparatus of claim 3 wherein means for sealing the introducer tube passageway with the elongate extension and swab therein is mounted on the introducer tube and is capable of receiving the elongate extension and swab therethrough.

6. The combination claim 4 wherein the cooperating means comprises a stopper on the elongate extension to engage the surface of the introducer tube and move lengthwise thereagainst to guide movement of the elongate extension and swab between the shielded and exposed positions.

7. The apparatus of claim 6 wherein the stopper includes means for sealing the introducer tube passageway with the elongate extension and swab therein.

8. The combination of claim 3 wherein the elongate includes means for limiting lengthwise movement of the swab in the exposed position.

9. The combination of claim 8 wherein the movement limiting means comprises a collar member on the elongate extension having an outside diameter slightly larger than the inner diameter of the introducer tube wall so that the collar member bears against the proximal end of the introducer tube when the swab is in the exposed position.

10. The combination of claim 9 wherein the proximal end of the tube comprises an enlarged annular end portion which bears against the collar member when the swab is in the exposed position.

11. The combination of claim 6 wherein the stopper is positioned between the swab and a collar on the elongate extension when the swab is in the exposed position.

12. The combination of claim 3 wherein the elongate extension and introducer tube are severable so that the introducer tube containing the elongate extension can be transferred to a culture medium without contaminating the culture sample.

13. The combination of claim 3 wherein the elongate extension is severable so that the introducer tube containing the elongate extension can be transferred to a culture medium without contaminating the culture sample.

14. An apparatus to take a culture sample from within a body cavity through a cannula having a through passageway with a diameter, said apparatus comprising:

an elongate extension having a swab thereon to pick up and transfer a culture sample from within a body cavity;

means for shielding the swab to facilitate introduction thereof into a body cavity with said shielding means comprising an introducer tube having a length and a proximal and distal end, said introducer tube having a wall defining an introducer tube through passageway wherein the wall of the introducer tube has an outside diameter that is less than the diameter of the through passageway on the cannula through which the introducer tube extends to allow the introducer tube to be directed to an operative position within the cannula wherein the swab can access a cavity from which a sample is to be taken with the swab; and cooperating means on the shielding means and at least one of the elongate extension and swab for guiding unobstructed relative movement thereof between a) a shielded position wherein transportation of the swab into and out of a body cavity is facilitated and b) an exposed position wherein the swab is exposed sufficiently to allow it to access a body cavity from which a culture sample is to be taken.

15. The apparatus of claim 14 further comprising means provided on the introducer tube for regulating the position of the introducer tube inserted in the cannula.

16. The apparatus of claim 15 wherein the regulating means comprises depth collar that bears against the cannula so that the introducer tube extends a predetermined distance into a body cavity.

17. An apparatus to take a culture sample from within a body cavity through a cannula, said apparatus comprising:

an elongate extension having a swab thereon to pick up and transfer a culture sample from within a body cavity;

means for shielding the swab to facilitate introduction thereof into a body cavity with said shielding means comprising an introducer tube having a length and a proximal and distal end, said introducer tube having a wall defining a through passageway;

cooperating means on the shielding means and at least one of the elongate extension and swab to guide unobstructed movement of the swab relative to the shielding means between a) a shielded position wherein transportation of the swab into and out of a body cavity is facilitated and b) an exposed position wherein the swab is exposed sufficiently to allow it to access a body cavity within a body from which a culture sample is to be taken; and means on the elongate extension for maintaining the swab in the shielded position and limiting lengthwise movement thereof relative to the introducer tube.

18. The apparatus of claim 17 wherein the maintaining means comprises a removable boss on the elongate extension having an outside diameter slightly larger than an inner diameter of the introducer tube wall thereby being capable of maintaining the swab in the shielded position.

19. The apparatus of claim 18 wherein the proximal end of the introducer tube comprises an enlarged annular end portion which bears against the removable boss so that the distal end of the introducer tube surrounds the swab in the shielded position.

20. The apparatus of claim 18 wherein the removable boss is positioned between a stopper on the elongate extension and means are provided on the elongate extension for limiting lengthwise movement of the swab in the exposed position.

21. An apparatus to take a culture sample from within a body cavity through a cannula, said apparatus comprising:
   an elongate extension having a swab thereon to pick up and transfer a culture sample from within a body cavity;
   means for shielding the swab to facilitate introduction thereof into a body cavity through the cannula wherein the shielding means comprises an introducer tube having a length and a proximal and a distal end, said introducer tube having a wall defining a through passageway;
   cooperating means on the shielding means and at least one of the elongate extension and swab to guide relative movement thereof between a) a shielded position wherein transportation of the swab into and out of a body cavity is facilitated and b) an exposed position wherein the swab is exposed sufficiently to allow it to access a body cavity within a body from which a culture sample is to be taken wherein the cooperating means comprises a surface on the introducer tube wall and a stopper on the elongate extension to engage the surface of the introducer tube wall and move lengthwise thereagainst to guide movement of the elongate extension and swab between the shielded and exposed positions wherein the stopper is positioned between the swab and a removable boss on the elongate extension when the swab is in the shielded position.

22. An apparatus to take a culture sample from within a body cavity through a cannula, said apparatus comprising:
   an elongate extension having a swab thereon to pick up and transfer a culture sample from within a body cavity wherein the elongate extension and swab are provided with at least one radio-opaque strip thereon so when the elongate extension and swab are in a body cavity they are detectable by an X-ray taken of a body cavity;
   means for shielding the swab to facilitate introduction thereof into a body cavity, said shielding means being movable into the cannula; and
   cooperating means on the shielding means and at least one of the elongate extension and swab to guide relative movement thereof between a) a shielded position wherein transportation of the swab into and out of a body cavity is facilitated and b) an exposed position wherein the swab is exposed sufficiently to allow it to access a body cavity from which a culture sample is to be taken.

23. An apparatus to take a culture sample from within a body cavity through a cannula, said apparatus comprising:
   an elongate extension having a swab thereon to pick up and transfer a culture sample from within a body cavity wherein the elongate extension is comprised of a non-heat conducting pyrogenic material;
   means for shielding the swab to facilitate introduction thereof into a body cavity; and
   cooperating means on the shielding means and at least one of the elongate extension and swab to guide unobstructed movement of the swab relative to the shielding means between a) a shielded position wherein transportation of the swab into and out of a body cavity is facilitated and b) an exposed position wherein the swab is exposed sufficiently to allow it to access a body cavity from which a culture sample is to be taken.

24. A method of obtaining a culture sample from within a body cavity through the cannula, said method comprising the steps of:
   inserting a cannula into a body cavity;
   introducing an elongate extension having a swab thereon into the cannula;
   exposing the swab through the cannula sufficiently to allow it to access a body cavity from which a culture sample is to be taken;
   isolating the culture sample from contaminants prior to withdrawal of the swab from the cannula; and
   transferring a sample from the body cavity to a culture medium without contaminating the culture sample.

25. The method of claim 24 further comprising the step of shielding the swab to facilitate introduction thereof into a body cavity.

26. The method of claim 24 further comprising the step of first directing the elongate extension and swab into an introducer tube having proximal and distal ends and a hollow passageway therethrough.

27. The method of claim 25 further comprising the step of providing an introducer tube to shield the swab, the introducer tube having proximal and distal ends and a hollow passageway therethrough with the elongate extension and swab therein.

28. The method of claim 25 including the step of isolating a culture sample from contaminants and transferring the culture sample from a body cavity to a culture medium without contaminating the culture sample by retracting the swab to a position within the distal introducer tube end and placing the elongate extension and the introducer tube in a culture medium.

29. The method of claim 26 including the step of exposing the swab to a body cavity by sliding the elongate extension lengthwise through the introducer tube, further including the step of providing a collar on the elongate extension so that the collar can abut the proximal introducer tube end when the swab is exposed.

30. The method of claim 28 further comprising the step of breaking the introducer tube and elongate extension therein leaving the swab in a culture medium.

31. The method of claim 28 further comprising the step of breaking the elongate extension leaving the swab in a culture medium.

32. A method of obtaining a culture sample from within a body cavity through a cannula, said method comprising the steps of:

directing an elongate extension having a swab thereon into an introducer tube having proximal and distal ends and a hollow passageway therethrough;

inserting the cannula into a body cavity;

introducing the elongate extension having the swab thereon and the introducer tube into the cannula;

exposing the swab through the cannula by removing a boss on the elongate extension bearing against the proximal tube end and sliding the elongate extension lengthwise through the introducer tube so that the swab is exposed to a body cavity from which a culture sample is to be taken;

isolating a culture sample from contaminants prior to withdrawal of the swab from the cannula; and transferring the culture sample from the body cavity to a culture medium without contaminating the culture sample.

33. A method for obtaining a culture sample from within a body cavity through a cannula, said method comprising the steps of sequentially:

inserting a cannula into a body cavity;

providing an introducer tube defining a hollow passageway and having proximal and distal ends;

directing an elongate extension having a swab thereon into the hollow passageway of the introducer tube;

inserting the introducer tube and elongate extension into the cannula;

removing a boss on the elongate extension bearing against the proximal introducer tube end;

sliding the elongate extension through the introducer tube passageway exposing the swab to a body cavity to place a culture sample on the swab;

retracting the swab from the body cavity into the distal introducer tube end without contaminating the culture sample;

transferring the introducer tube and elongate extension into a culture medium; and snapping the introducer tube and elongate extension leaving the swab in the culture medium.

* * * * *